United States Patent
Hori et al.

(10) Patent No.: US 9,815,779 B2
(45) Date of Patent: Nov. 14, 2017

(54) METHOD FOR PRODUCING INTERNAL OLEFIN SULFONATE

(71) Applicant: KAO CORPORATION, Tokyo (JP)

(72) Inventors: Hiroshi Hori, Wakayama (JP); Yohei Yoshikawa, Wakayama (JP); Yoshinori Mitsuda, Wakayama (JP); Toku Fujioka, Brookline, MA (US); Yoshifumi Nishimoto, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/108,087

(22) PCT Filed: Nov. 27, 2014

(86) PCT No.: PCT/JP2014/081354
§ 371 (c)(1),
(2) Date: Jun. 24, 2016

(87) PCT Pub. No.: WO2015/098415
PCT Pub. Date: Jul. 2, 2015

(65) Prior Publication Data
US 2016/0332961 A1    Nov. 17, 2016

(30) Foreign Application Priority Data
Dec. 27, 2013    (JP) .................................. 2013-272379

(51) Int. Cl.
*C07C 303/32*    (2006.01)
*C11D 1/14*    (2006.01)

(52) U.S. Cl.
CPC .............. *C07C 303/32* (2013.01); *C11D 1/14* (2013.01); *C11D 1/143* (2013.01)

(58) Field of Classification Search
None
See application file for complete search history.

(56) References Cited

U.S. PATENT DOCUMENTS

| | | | |
|---|---|---|---|
| 4,183,867 A | 1/1980 | Sekiguchi et al. | |
| 4,507,223 A * | 3/1985 | Tano ...................... | C09K 8/584 507/259 |
| 5,529,722 A | 6/1996 | Aouad et al. | |

FOREIGN PATENT DOCUMENTS

| | | |
|---|---|---|
| CN | 102504791 A | 6/2012 |
| EP | 0 351 928 A1 | 1/1990 |
| EP | 2 990 395 A1 | 3/2016 |
| JP | 52-33096 | 8/1977 |
| JP | 2-73051 A | 3/1990 |
| JP | 2000-96084 A | 4/2000 |
| JP | 2001-114749 A | 4/2001 |
| JP | 2003-81935 A | 3/2003 |
| JP | 2003-147390 A | 5/2003 |
| WO | WO 2008/078609 A1 | 7/2008 |
| WO | WO 2013/093075 A1 | 6/2013 |
| WO | WO 2013/131766 A1 * | 9/2013 ........... C07C 309/20 |
| WO | WO 2014/175359 A1 | 10/2014 |

OTHER PUBLICATIONS

International Search Report, issued in PCT/JP2014/081354, dated Feb. 17, 2015.
International Preliminary Report on Patentability and Written Opinion of the International Searching Authority (Forms PCT/IB338, PCT/IB/373, and PCT/ISA/237) for International Application No. PCT/JP2014/081354, dated Jul. 7, 2016.
Chinese Office Action and Chinese Search Report, dated Jan. 13, 2017, for Chinese Application No. 201480071238.1.
Extended European Search Report dated Jul. 18, 2017, for European Application No. 14875839.4.

* cited by examiner

*Primary Examiner* — Yate K Cutliff
(74) *Attorney, Agent, or Firm* — Birch, Stewart, Kolasch & Birch, LLP

(57) ABSTRACT

The present invention provides a method for producing a high-quality internal olefin sulfonate in which the content of any internal olefin and inorganic substance is small. This method for producing an internal olefin sulfonate, comprising: a sulfonating step of causing an internal olefin to react with sulfur trioxide to yield a sulfonated internal olefin; a neutralizing step of mixing the resultant sulfonated internal olefin with an aqueous alkaline solution at 40° C. or lower to yield a mixture, and applying shearing force to the mixture until the particle diameter of oil droplets of an oily product of the mixture turns to 10 μm or less to yield a neutralized product; and a hydrolyzing step of hydrolyzing the resultant neutralized product.

15 Claims, No Drawings

METHOD FOR PRODUCING INTERNAL OLEFIN SULFONATE

TECHNICAL FIELD

The present invention relates to a method for producing an internal olefin sulfonate.

BACKGROUND ART

Conventionally, anionic surfactants, particularly, alkylsulfates and polyoxyalkylene alkyl ether sulfates are widely used as washing components for home use and industrial use since the surfactants are excellent in washing power and foaming power. As one of the anionic surfactants, a report has been made about an olefin sulfonate, particularly, an internal olefin sulfonate obtained using, as a raw material, an internal olefin, which has a double bond not at any terminal of the olefin but at an inside thereof.

Such an internal olefin sulfonate is generally obtained by causing an internal olefin to react with a gaseous-sulfur-trioxide-containing gas to sulfate the olefin, neutralizing the resultant sulfonated internal olefin, and further hydrolyzing the neutralized product. It is known that this internal olefin sulfonate is good in biodegradability and others. However, as compared with general-purpose surfactants, such as polyoxyalkylene alkyl ether sulfates, the internal olefin sulfonate has not yet been sufficient in basic performances for washing agents, typical examples of the performances being foaming performance and foam property. Thus, the internal olefin sulfonate has been desired to be further improved. In order to improve the basic performances for washing agents, it is important to decrease internal olefins and an inorganic substance which are each by-produced in a process for producing the sulfonate.

It has been understood that the internal olefins and the inorganic substance (sodium sulfate) are generated by reverse-reactions of β-sultone, which is a reaction intermediate. JP-A-2-073051 describes an internal olefin sulfonate producing method for producing an internal olefin sulfonate having a low free-oil content, a low inorganic-sulfate content and a bright color. This method includes: causing an internal olefin to react with a sulfonating agent at a specific molar ratio in a thin-film reactor while this reaction system is cooled through a cooling means having a temperature not higher than 35° C.; neutralizing the reaction product; and then hydrolyzing the product. This publication also states that at the time of producing an internal olefin sulfonate derived from an olefin having more than 14 carbon atoms, it is necessary to attain a close mixing of the reaction product with an aqueous base in the neutralization and the hydrolysis.

SUMMARY OF THE INVENTION

A method for producing an internal olefin sulfonate of the present invention, comprising:

a sulfonating step of causing an internal olefin to react with sulfur trioxide to yield a sulfonated internal olefin;

a neutralizing step of mixing the resultant sulfonated internal olefin with an aqueous alkaline solution at 40° C. or lower to yield a mixture, and applying shearing force to the mixture until the particle diameter of oil droplets of an oily product of the mixture turns to 10 μm or less to yield a neutralized product; and a hydrolyzing step of hydrolyzing the resultant neutralized product.

MODE FOR CARRYING OUT THE INVENTION

Conventional techniques are insufficient in preventing the by-production of any internal olefin and inorganic salt.

The present invention provides a method for producing a high-quality internal olefin sulfonate in which the content of any internal olefin and inorganic substance is small.

The inventors have found out that the by-production of any internal olefin and inorganic salt can be restrained by making oil droplets of an oily product fine in a neutralizing step, under a low temperature condition, until the particle diameter of the oil droplets turns to 10 μm or less, so that a high-quality internal olefin sulfonate is obtained. Thus, the present invention has been accomplished.

That is, the present invention relates to a method for producing an internal olefin sulfonate, comprising:

a sulfonating step of causing an internal olefin to react with sulfur trioxide to yield a sulfonated internal olefin;

a neutralizing step of mixing the resultant sulfonated internal olefin with an aqueous alkaline solution at 40° C. or lower to yield a mixture, and applying shearing force to the mixture until the particle diameter of oil droplets of an oily product of the mixture turns to 10 μm or less to yield a neutralized product; and a hydrolyzing step of hydrolyzing the resultant neutralized product.

The present invention makes it possible to restrain the by-production of any internal olefin and inorganic salt to produce a high-quality internal olefin sulfonate effectively.

Hereinafter, the present invention will be described in detail.

A method for producing an internal olefin sulfonate of the present invention, comprising:

a sulfonating step of causing an internal olefin to react with sulfur trioxide to yield a sulfonated internal olefin;

a neutralizing step of mixing the resultant sulfonated internal olefin with an aqueous alkaline solution at 40° C. or lower to yield a mixture, and applying shearing force to the mixture until the particle diameter of oil droplets of an oily product of the mixture turns to 10 μm or less to yield a neutralized product; and a hydrolyzing step of hydrolyzing the resultant neutralized product.

<Sulfonating Step>

The sulfonating step is a step of causing an internal olefin to react with sulfur trioxide to yield a sulfonated internal olefin.

The internal olefin is an olefin having, inside the olefin chain thereof, a double bond. The internal olefin may include a trace amount of the so-called α-olefin, which has, at a 1-position of the carbon chain thereof, a double bond.

The internal olefin preferably includes an internal olefin isomer which has, at a C2 position thereof, a double bond in a proportion that is preferably 48% or less, more preferably 35% or less by mass from the viewpoint of the washing performance and foaming performance of the internal olefin sulfonate when the sulfonate is used as a washing agent. The proportion of this isomer is preferably 10% or more, more preferably 15% or more by mass from the viewpoint of the productivity of the internal olefin.

The number of carbon atoms in the internal olefin is preferably 10 or more, more preferably 12 or more, even more preferably 14 or more, and is also preferably 22 or less, more preferably 18 or less from the viewpoint of the washing performance and others of the internal olefin sulfonate when the sulfonate is used for a washing agent.

One type of internal olefin may be used alone, or two or more types thereof may be used in combination. In the case of the use of two or more types of internal olefin in combination, the following is preferably used from the viewpoint of the washing performance and others of the internal olefin sulfonate when the sulfonate is used for a washing agent: a combination of an internal olefin having 16 carbon atoms with an internal olefin having 18 carbon atoms.

The internal olefin can be produced by a known method, for example, a method described in International Publication No. 2011/052732.

Sulfur trioxide is caused to react preferably as sulfur trioxide gas from the viewpoint of an improvement in the reactivity thereof.

The use amount of sulfur trioxide is preferably 0.8 mol or more, more preferably 0.9 mol or more, even more preferably 0.95 mol or more per mole of the internal olefin to improve the yield of the sulfonated internal olefin and improve the reactivity. The amount is preferably 1.2 mol or less, more preferably 1.1 mol or less, even more preferably 1.05 mol or less from the viewpoint of economy and prevention of the coloring of the sulfonated internal olefin.

In order to cause the internal olefin in a liquid form to react with sulfur trioxide in a gaseous form, it is preferred to use, for the sulfonating reaction, a thin-film sulfonation reactor equipped with an external jacket.

The treating temperature in the sulfonating step is preferably 0° C. or higher to prevent the solidification of sulfur trioxide and the sulfonated internal olefin, and is also preferably 50° C. or lower to restrain the coloring of the sulfonated internal olefin.

The sulfonating reaction is exothermic reaction; thus, it is preferred to fit an external jacket to the reactor, and pass cooling water thereinto to cool the reactor. The temperature of the cooling water, which is passed into the external jacket of the reactor, is preferably 0° C. or higher to improve the reaction velocity. The temperature is also preferably 30° C. or lower, more preferably 20° C. or lower to restrain any by-reaction to decrease impurities, such as a fraction of the internal olefin and any inorganic salt in the finally obtained internal olefin sulfonate.

The rate of the sulfonating reaction is preferably 95% or more, more preferably 97% or more, even more preferably 98% or more to improve the yield of the sulfonated internal olefin. The rate is also preferably 99.8% or less to restrain the coloring of the sulfonated internal olefin caused by an excessive fraction of $SO_3$.

<Neutralizing Step>

The neutralizing step is a step of mixing the sulfonated internal olefin with an aqueous alkaline solution at 40° C. or lower to yield a mixture, and applying shearing force to the resultant mixture until the particle diameter of oil droplets of an oily product of the mixture turns to 10 μm or less, thereby yielding a neutralized product.

The alkaline compound used for the neutralization may be an inorganic alkaline compound or an organic alkaline compound. Examples of the inorganic alkaline compound may be alkali metal hydroxides such as sodium hydroxide and potassium hydroxide, and alkali metal carbonates such as sodium carbonate and potassium carbonate. Examples of the organic alkaline compound may be ammonia, and amine compounds having 1 to 6 carbon atoms, such as 2-aminoethanol.

The alkaline compound is preferably an inorganic alkaline compound, more preferably an alkali metal hydroxide, even more preferably at least one selected from sodium hydroxide and potassium hydroxide, even more preferably sodium hydroxide from the viewpoint of the availability thereof and economy.

The concentration in the aqueous alkaline solution is preferably 1% or more, more preferably 4.5% or more, even more preferably 7% or more, even more preferably 10% or more, even more preferably 12% or more by mass from the viewpoint of economy and prevention of the production of impurities, such as the internal olefin and inorganic salts. The concentration is also preferably 30% or less, more preferably 25% or less, even more preferably 23% or less, even more preferably 20% or less, even more preferably 15% or less by mass from the viewpoint of the productivity of the target in the hydrolyzing step.

The addition amount of the alkaline compound is preferably 1 time or more, more preferably 1.03 times or more by mole relative to the sulfonate group to restrain the production of impurities, such as the internal olefin and inorganic salts, and improve the reactivity. The amount is also preferably 2.5 times or less, more preferably 2.0 times or less, even more preferably 1.5 times or less by mole from the viewpoint of economy and prevention of the production of impurities, such as the internal olefin and inorganic salts.

In the neutralizing step, the concentration of the sulfonated internal olefin in the mixture is preferably 15% or more, more preferably 30% or more, even more preferably 40% or more, even more preferably 45% or more, even more preferably 48% or more, even more preferably 50% or more by mass to restrain the production of impurities, such as the internal olefin and inorganic salts, caused by decomposition reaction of the sulfonated internal olefin. The concentration is preferably 75% or less, more preferably 70% or less, even more preferably 65% or less, even more preferably 60% or less by mass to restrain the heat of neutralization. The concentration of the sulfonated internal olefin in the neutralizing step denotes the total of the following: the concentration of a non-neutralized fraction of the sulfonated internal olefin; and the concentration of the neutralized product of the sulfonated internal olefin in terms of that of the sulfonated internal olefin.

The temperature when the sulfonated internal olefin is mixed with the aqueous alkaline solution in the neutralizing step, and the temperature at time of the neutralizing reaction are each 40° C. or lower, preferably 35° C. or lower, more preferably 30° C. or lower, even more preferably 25° C. or lower to restrain the production of impurities, such as the internal olefin and inorganic salts, through by-reactions. The temperatures are also each preferably 0° C. or higher, more preferably 10° C. or higher, even more preferably 15° C. or higher, even more preferably 20° C. or higher to improve the reactivity.

In the neutralizing step, in order to improve the reactivity to restrain the production of impurities, such as the internal olefin and inorganic salts, through by-reactions, shearing force is applied to the mixture at 40° C. or lower until the particle diameter of oil droplets of an oily product of the mixture turns to 10 μm or less. The shearing force is applied until the particle diameter of the oil droplets of the oily product turns preferably to 6.5 μm or less, more preferably to 4.0 μm or less, even more preferably to 3.8 μm or less, even more preferably to 2.5 μm or less, even more preferably to 2.0 μm or less, even more preferably to 1.8 μm or less. The lower limit of the particle diameter of the oil droplets is not particularly limited, and is preferably 0.1 μm or more, more preferably 0.5 µm or more, even more preferably 1 µm or more from the viewpoint of the productivity. By applying the shearing force to the oily product, both of a reduction of the oily product in size and the neutralization advance so that a neutralized product is finally yielded. The particle diameter of the oil droplets of the oily product is measured, specifically, by a method described in item "EXAMPLES".

The sulfonated internal olefin mainly contains sultone, which is insoluble in water, to turn into a two-phase system of oil and water initially in the neutralizing step. By applying the shearing force thereto to make the oily product fine rapidly, an internal olefin sulfonate can be obtained in which the olefin as the starting material, and by-products such as sulfates are small in amount. A reason therefor is presumed as follows. The neutralizing reaction is caused in the interface. A reverse reaction of the sulfonation is caused in the oil phase. Accordingly, by increasing the area of the interface, the proportion of the target neutralizing reaction can be raised so that any side reaction can be restrained.

In the neutralizing step, a mixer of any type may be used as far as the mixer is capable of mixing the sulfonated internal olefin effectively with the aqueous alkaline solution and applying shearing force to the oily product. Examples of this mixer include a stationary type mixer, a collision type mixer, an agitating impeller type mixer, and a vibration type mixer. The stationary type mixer is, for example, a static mixer manufactured by Noritake Co., Ltd. The collision type mixer is, for example, a high-pressure emulsifying machine manufactured by Nanomizer Inc. The agitating impeller type mixer is, for example, a Milder manufactured by Matsubo Corporation, or a Homo Mixer manufactured by PRIMIX Corporation. Out of these examples, the agitating impeller type mixer is preferred from the viewpoint of machine costs.

When the agitating impeller type mixer is used, the agitating speed of the agitating machine is preferably 5 m/s or more, more preferably 10 m/s or more, even more preferably 20 m/s or more to restrain the production of impurities such as the internal olefin and inorganic salts. The agitating speed is preferably 30 m/s or less, more preferably 27.5 m/s or less, even more preferably 25 m/s or less to restrain the generation of heat. The agitating speed is the speed of the tip of the agitating impeller, and is represented by the following: 2×"the circular constant"×"the radius of the agitating impeller"×"the number of rotations of the agitating impeller per unit time".

When the agitating impeller type mixer is used, the rate of the shearing given to the oily product is preferably $2\times10^3$ $s^{-1}$ or more, more preferably $5\times10^3$ $s^{-1}$ or more, even more preferably $1\times10^4$ $s^{-1}$ or more, even more preferably $2\times10^4$ $s^{-1}$ or more to make the oily product finer. The rate is also preferably $5\times10^4$ $s^{-1}$ or less, more preferably $3.8\times10^4$ $s^{-1}$ or less, even more preferably $2.5\times10^4$ $s^{-1}$ or less to restrain the heat of neutralization.

The neutralizing step can be performed by the so-called continuous method, in which while a loop-type reactor is used to circulate the reaction liquid, the sulfonated internal olefin and the aqueous alkaline solution are added thereto, and simultaneously the reaction liquid is removed therefrom. From the viewpoint of prevention of the production of by-products and the productivity, the neutralizing step is performed preferably by the continuous method, and is performed more preferably using a loop-type reactor.

In the neutralizing step, a period for the neutralization is preferably 5 minutes or longer, more preferably 10 minutes or longer, even more preferably 15 minutes or longer to conduct the neutralizing reaction sufficiently. The period is preferably 100 minutes or shorter, more preferably 50 minutes or shorter, even more preferably 20 minutes or shorter to improve the productivity.

In the case of the continuous method, the neutralizing period can be represented as the mean residence time obtained by dividing the volume of the loop-type reactor by the total addition amount of the sulfonated internal olefin and the aqueous alkaline solution per unit period. The mean residence time is preferably 8 minutes or longer, more preferably 10 minutes or longer, even more preferably 12 minutes or longer to restrain the heat of neutralization. The period is preferably 60 minutes or shorter, more preferably 30 minutes or shorter, even more preferably 20 minutes or shorter, even more preferably 15 minutes or shorter to improve the productivity. In the case of the continuous method, the circulatory ratio of the reaction liquid is preferably 3 times or more, more preferably 6 times or more, even more preferably 9 times or more to improve the reactivity. The circulatory ratio is also preferably 30 times or less, more preferably 20 times or less, even more preferably 15 times or less to restrain a rise in the pressure in the reactor. The circulatory ratio is the ratio of the amount of the entire contents circulating in the reactor to the flowing amount of the reaction liquid charged into the reactor, and is represented by the following: "the total circulating amount in the reactor"/"the amount charged into the reactor".

In the neutralizing step, the following maybe caused to coexist with the mixture: a water-soluble organic solvent such as an alcohol or acetone, and/or a surfactant such as a polyoxyethylene alkyl ether or an α-olefinsulfonic acid. It is preferred not to use the coexisting product(s) since the product(s) is/are denatured at the time of the neutralizing reaction, remain(s) in the final product, or give(s) a burden to the step of purifying the final product. In the case of using the product (s), the product (s) is/are used in the mixed liquid in a proportion of preferably 20% or less, more preferably 10% or less, even more preferably 2% or less, even more preferably 1% or less by mass.

<Hydrolyzing Step>

The hydrolyzing step is a step of hydrolyzing the resultant neutralized product.

In the hydrolyzing step, the temperature at the time of the hydrolysis is preferably 120° C. or higher, more preferably 140° C. or higher, even more preferably 160° C. or higher to improve the reactivity. The temperature is also preferably 220° C. or lower, more preferably 180° C. or lower to restrain the decomposition of the product.

The hydrolysis reaction may be conducted in a batch reactor, or in a continuous reactor.

The treating period in the hydrolyzing step is preferably 30 minutes or longer, more preferably 45 minutes or longer to complete the reaction. The period is also preferably 4 hours or shorter, more preferably 3 hours or shorter, even more preferably 2 hours or shorter, even more preferably 90 minutes or shorter to improve the productivity.

The concentration in the aqueous internal olefin sulfonate solution obtained through the hydrolyzing step is preferably 15% or more, more preferably 30% or more, even more preferably 40% or more, even more preferably 45% or more, even more preferably 48% or more, even more preferably 50% or more by mass from the viewpoint of the productivity. The concentration is also preferably 75% or less, more preferably 70% or less, even more preferably 65% or less, even more preferably 60% or less by mass from the viewpoint of the viscosity of the aqueous solution, and others.

The internal olefin sulfonate is usable as it is for various purposes. The sulfonate may be further subjected to purifications, such as desalting and decoloring.

The internal olefin sulfonate yielded by the producing method of the present invention is good in purity and hue. Thus, the sulfonate is usable for various articles, such as body washing agents, shampoos, clothing washing agents, and tableware washing agents.

The present invention discloses, besides the above, the following embodiments.

<1>

A method for producing an internal olefin sulfonate, comprising:

a sulfonating step of causing an internal olefin to react with sulfur trioxide to yield a sulfonated internal olefin;

a neutralizing step of mixing the resultant sulfonated internal olefin with an aqueous alkaline solution at 40° C. or lower to yield a mixture, and applying shearing force to the mixture until the particle diameter of oil droplets of an oily product of the mixture turns to 10 μm or less to yield a neutralized product; and a hydrolyzing step of hydrolyzing the resultant neutralized product.

<2>

The method for producing an internal olefin sulfonate according to item <1>, wherein in the neutralizing step, the mixing of the sulfonated internal olefin with the aqueous alkaline solution is performed preferably at 35° C. or lower, more preferably at 30° C. or lower, even more preferably 25° C. or lower, and preferably at 0° C. or higher, more preferably at 10° C. or higher, even more preferably 15° C. or higher, even more preferably 20° C. or higher.

<3>

The method for producing an internal olefin sulfonate according to item <1> or <2>, wherein in the neutralizing step, the mixing of the sulfonated internal olefin with the aqueous alkaline solution is performed until the particle diameter of the oil droplets of the oily product turns preferably to 6.5 μm or less, more preferably to 4.0 μm or less, even more preferably to 3.8 μm or less, even more preferably to 2.5 μm, even more preferably to 2.0 μm or less, even more preferably to 1.8 μm or less, and preferably to 0.1 μm or more, more preferably to 0.5 μm or more, even more preferably to 1 μm or more.

<4>

The method for producing an internal olefin sulfonate according to any one of items <1> to <3>, wherein in the neutralizing step, the concentration of the sulfonated internal olefin is preferably 15% or more, more preferably 30% or more, even more preferably 40% or more, even more preferably 45% or more, even more preferably 48% or more, even more preferably 50% or more by mass, and preferably 75% or less, more preferably 70% or less, even more preferably 65% or less, even more preferably 60% or less by mass.

<5>

The method for producing an internal olefin sulfonate according to any one of items <1> to <4>, wherein in the neutralizing step, a means for applying the shearing force is an agitating machine.

<6>

The method for producing an internal olefin sulfonate according to item <5>, wherein the agitating speed of the agitating machine is preferably 5 m/s or more, more preferably 10 m/s or more, even more preferably 15 m/s or more, even more preferably 20 m/s or more, and preferably 30 m/s or less, more preferably 27.5 m/s or less, even more preferably 25 m/s or less.

<7>

The method for producing an internal olefin sulfonate according to any one of items <1> to <6>, wherein in the neutralizing step, a period for the neutralization is preferably 5 minutes or longer, more preferably 10 minutes or longer, even more preferably 15 minutes or longer, and preferably 100 minutes or shorter, more preferably 50 minutes or shorter, even more preferably 20 minutes or shorter.

<8>

The method for producing an internal olefin sulfonate according to any one of items <1> to <7>, wherein the neutralizing step is performed preferably by the continuous method, and is performed more preferably using a loop-type reactor.

<9>

The method for producing an internal olefin sulfonate according to item <8>, wherein in the neutralizing step, a period for the neutralization is preferably 8 minutes or longer, more preferably 10 minutes or longer, even more preferably 12 minutes or longer, and preferably 60 minutes or shorter, more preferably 30 minutes or shorter, even more preferably 20 minutes or shorter, even more preferably 15 minutes or shorter to improve the productivity.

<10>

The method for producing an internal olefin sulfonate according to item <8> or <9>, wherein the circulatory ratio of the reaction liquid is preferably 3 times or more, more preferably 6 times or more, even more preferably 9 times or more, and preferably 30 times or less, more preferably 20 times or less, even more preferably 15 times or less.

<11>

The method for producing an internal olefin sulfonate according to any one of items <1> to <10>, wherein an alkaline compound used in the neutralizing step is preferably an inorganic alkaline compound, more preferably an alkali metal hydroxide, even more preferably at least one selected from sodium hydroxide and potassium hydroxide, even more preferably sodium hydroxide.

<12>

The method for producing an internal olefin sulfonate according to any one of items <1> to <11>, wherein in the neutralizing step, the concentration in the aqueous alkaline solution is preferably 1% or more, more preferably 4.5% or more, even more preferably 7% or more, even more preferably 10% or more, even more preferably 12% or more by mass, and preferably 30% or less, more preferably 25% or less, even more preferably 23% or less, even more preferably 20% or less, even more preferably 15% or less by mass.

<13>

The method for producing an internal olefin sulfonate according to any one of items <1> to <12>, wherein in the neutralizing step, the addition amount of the alkaline compound is preferably 1 time or more, more preferably 1.03 times or more by mole relative to the sulfonate group, and preferably 2.5 times or less, more preferably 2.0 times or less, even more preferably 1.5 times or less by mole.

<14>

The method for producing an internal olefin sulfonate according to any one of items <1> to <13>, wherein the content by percentage of an internal olefin isomer which has, at a C2 position thereof, a double bond in the internal olefin is preferably 48% or less, more preferably 35% or less by mass, and preferably 10% or more, more preferably 15% or more by mass.

<15>

The method for producing an internal olefin sulfonate according to any one of items <1> to <14>, wherein the number of carbon atoms in the internal olefin is preferably 10 or more, more preferably 12 or more, even more preferably 14 or more, and preferably 22 or less, more preferably 18 or less.

<16>

The method for producing an internal olefin sulfonate according to any one of items <1> to <15>, wherein one type of internal olefin is used alone, or two or more types thereof are used in combination, and a combination of an internal olefin having 16 carbon atoms with an internal olefin having 18 carbon atoms is preferably used.

<17>

The method for producing an internal olefin sulfonate according to any one of items <1> to <16>, wherein at the time of the sulfonation, the temperature of reactor-cooling water is preferably 0° C. or higher, and preferably 30° C. or lower, more preferably 20° C. or lower.

<18>

The method for producing an internal olefin sulfonate according to any one of items <1> to <17>, wherein the use amount of sulfur trioxide is preferably 0.8 mol or more, more preferably 0.9 mol or more, even more preferably 0.95 mol or more per mole of the internal olefin, and preferably 1.2 mol or less, more preferably 1.1 mol or less, even more preferably 1.05 mol or less.

<19>

The method for producing an internal olefin sulfonate according to any one of items <1> to <18>, wherein the temperature at the time of the hydrolysis is preferably 120° C. or higher, more preferably 140° C. or higher, even more preferably 160° C. or higher, and preferably 220° C. or lower, more preferably 180° C. or lower.

<20>

The method for producing an internal olefin sulfonate according to any one of items <1> to <19>, wherein the concentration in the aqueous internal olefin sulfonate solution obtained through the hydrolyzing step is preferably 15% or more, more preferably 30% or more, even more preferably 40% or more, even more preferably 45% or more, even more preferably 48% or more, even more preferably 50% or more by mass, and preferably 75% or less, more preferably 70% or less, even more preferably 65% or less, even more preferably 60% or less by mass.

EXAMPLES

Hereinafter, the present invention will be specifically described on the basis of Examples. In Tables, the content of each component is shown in terms of the unit "% by mass" unless otherwise specified. Various measuring methods are as described below.

<Method for Measuring Double Bond Position of Internal Olefin>

Double bond positions of internal olefin were measured by gas chromatography (hereinafter abbreviated to GC). Specifically, dimethyl disulfide was caused to react with internal olefin to prepare dithionated derivatives thereof. Subsequently, individual components of the resultant derivatives were separated from each other by GC. From the individual peak areas, double bond positions of internal olefin were analyzed. Instruments and analyzing conditions used for the measurement were as follows: GC instrument "HP6890" (manufactured by Hewlett Packard Company), a column "Ultra-Alloy-1HT capillary column" (manufactured by Frontier Laboratories Ltd.; 30 m×250 μm×0.15 μm), and a detector (hydrogen flame ionization detector (FID)); and an injection temperature of 300° C., a detector temperature of 350° C., and a He flow rate of 4.6 mL/min.

<Method for Measuring Content of Internal Olefin Contained in Internal Olefin Sulfonate>

The content of internal olefin contained in internal olefin sulfonate was determined by GC. Specifically, ethanol and petroleum ether were added to an aqueous solution of internal olefin sulfonate, and then the resultant was subjected to extraction to yield internal olefin in a phase of the petroleum ether. From the areas of GC peaks thereof, internal olefin was quantitatively determined. Instruments and analyzing conditions used for the measurement were as follows: GC instrument "AGILENT TECHNOLOGIES 6850" (manufactured by Agilent Technologies, Inc.), a column "Ultra-Alloy-1HT capillary column" (manufactured by Frontier Laboratories Ltd.; 15 m×250 μm×0.15 μm), and a detector (hydrogen flame ionization detector (FID)); and an injection temperature of 300° C., a detector temperature of 350° C., and a He flow rate of 3.8 mL/min.

<Method for Measuring Content of Inorganic Salt Contained in Internal Olefin Sulfonate>

The content of an inorganic salt was determined by potentiometric titration or neutralization titration. Specifically, the content of $Na_2SO_4$ was quantitatively determined by obtaining the amount of sulfate ions ($SO_4^{2-}$) by potentiometric titration.

<Method for Measuring Particle Diameter of Oil Droplets>

A scattering particle size distribution measuring instrument "LA-920" (manufactured by HORIBA Ltd.) was used to measure the particle diameter of oil droplets of an oily product in the neutralizing step. Specifically, the oily product that has turned into oil droplets was appropriately sampled, and the oily product was promptly diluted and cooled with ion exchange water the temperature of which was room temperature. Thereafter, the particle size distribution of the oily product was calculated. From the average of the respective area values of the resultant peaks, the oil droplet particle diameter (volume-average median diameter) was measured.

<Method for Producing Internal Olefin>

Production Example A

Synthesis of Internal Olefin having 16 Carbon Atoms (C2 Position: 16.5% by Mass)

Into a flask equipped with a stirrer were charged 7000 g (28.9 mol) of 1-hexadecanol "KALCOL 6098" (manufactured by Kao Corp.), and 700 g (10% by mass of the alcohol as the starting material) of γ-alumina (manufactured by STREM Chemicals, Inc.) as a solid acid catalyst. The alcohol was caused to react under stirring at 280° C. for 5 hours while nitrogen (7000 mL/min.) was caused to flow into the system. After the end of the reaction, the conversion rate of the alcohol was 100%. The purity of the resultant C16 internal olefin was 99.7%. The resultant crude internal olefin was placed into a flask for distillation, and distilled at 136 to 160° C. and 4.0 mmHg to yield an internal olefin having 16 carbon atoms and an olefin purity of 100%. The double bond distribution of the resultant internal olefin was as follows: C1 position: 0.5% by mass; C2 position: 16.5% by mass; C3 position: 15.4% by mass; C4 position: 16.4% by mass; C5 position: 17.2% by mass; C6 position: 14.2% by mass; and C7 and C8 positions: 19.8% by mass in total.

Production Example B

Synthesis of Internal Olefin having 18 Carbon atoms (C2 Position: 16.9% by Mass)

Into a flask equipped with a stirrer were charged 7000 g (25.9 mol) of 1-octadecanol "KALCOL 8098" (manufactured by Kao Corp.), and 1050 g (15% by mass of the alcohol as the starting material) of γ-alumina (manufactured by STREM Chemicals, Inc.) as a solid acid catalyst. The alcohol was caused to react under stirring at 285° C. for 13 hours while nitrogen (7000 mL/min.) was caused to flow into the system. After the end of the reaction, the conversion rate of the alcohol was 100%. The purity of the resultant C18 internal olefin was 98.5%. The resultant crude internal olefin was placed into a flask for distillation, and distilled at 148 to 158° C. and 0.5 mmHg to yield an internal olefin having 18 carbon atoms and an olefin purity of 100%. The double bond distribution of the resultant internal olefin was as follows: C1 position: 0.7% by mass; C2 position: 16.9% by mass; C3 position: 15.9% by mass; C4 position: 16.0% by mass; C5 position: 14.6% by mass; C6 position: 11.2% by mass; C7 position: 10.1% by mass; and C8 and C9 positions : 14.6% by mass in total.

Production Example C

Preparation of Internal Olefins having 16/18 Carbon Atoms (Ratio by Mass: 74.0/26.0)

Internal olefins having 16 carbon atoms and 18 carbon atoms, respectively, were yielded in the same ways as in Production Examples A and B. 11.1 kg of the resultant C16 olefin was mixed with 3.9 kg of the resultant C18 internal olefin to yield 15 kg of C16/C18 internal olefins (ratio by mass: 74.0/26.0). The double bond distribution of the resultant internal olefins was as follows: C1 position: 0.6% by mass; C2 position: 16.6% by mass; C3 position: 15.5% by mass; C4 position: 16.3% by mass; C5 position: 16.6% by mass; C6 position: 13.4% by mass; C7 position: 9.9% by mass; and C8 and C9 positions: 11.1% by mass in total.

Production Example D

Synthesis of Internal Olefin having 16 Carbon Atoms (C2 Position: 30.7% by Mass)

Into a flask equipped with a stirrer were charged 7000 g (28.9 mol) of 1-hexadecanol "KALCOL 6098" (manufactured by Kao Corp.), and 700 g (10% by mass of the alcohol as the starting material) of γ-alumina (manufactured by STREM Chemicals, Inc.) as a solid acid catalyst. The alcohol was caused to react under stirring at 280° C. for 3 hours while nitrogen (7000 mL/min.) was caused to flow into the system. After the end of the reaction, the conversion rate of the alcohol was 100%. The purity of the resultant C16 internal olefin was 99.6%. The resultant crude internal olefin was placed into a flask for distillation, and distilled at 136 to 160° C. and 4.0 mmHg to yield an internal olefin having 16 carbon atoms and an olefin purity of 100%. The double bond distribution of the resultant internal olefin was as follows: C1 position: 0.6% by mass; C2 position: 30.7% by mass; C3 position: 26.1% by mass; C4 position: 18.8% by mass; C5 position: 10.5% by mass; 06 position: 6.7% by mass; and 07 and C8 positions: 6.6% by mass in total.

Production Example E

Synthesis of Internal Olefin having 18 Carbon atoms (C2 Position: 25.0% by Mass)

Into a flask equipped with a stirrer were charged 7000 g (25.9 mol) of 1-octadecanol "KALCOL 8098" (manufactured by Kao Corp.), and 700 g (10% by mass of the alcohol as the starting material) of γ-alumina (manufactured by STREM Chemicals, Inc.) as a solid acid catalyst. The alcohol was caused to react under stirring at 280° C. for 10 hours while nitrogen (7000 mL/min.) was caused to flow into the system. After the end of the reaction, the conversion rate of the alcohol was 100%. The purity of the resultant C18 internal olefin was 98.2%. The resultant crude internal olefin was placed into a flask for distillation, and distilled at 148 to 158° C. and 0.5 mmHg to yield an internal olefin having 18 carbon atoms and an olefin purity of 100%. The double bond distribution of the resultant internal olefin was as follows: C1 position: 0.5% by mass; 02 position: 25.0% by mass; C3 position: 22.8% by mass; 04 position: 19.1% by mass; C5 position: 14.0% by mass; 06 position: 7.4% by mass; C7 position: 5.4% by mass; and C8 and C9 positions: 5.8% by mass in total.

Production Example F

Preparation of Internal Olefins having 16/18 Carbon Atoms (Ratio by Mass: 79.4/20.6)

Internal olefins having 16 carbon atoms and 18 carbon atoms, respectively, were yielded in the same ways as in Production Examples D and E. 11.9 kg of the resultant C16 olefin was mixed with 3.1 kg of the resultant C18 internal olefin to yield 15 kg of C16/C18 internal olefins (ratio by mass: 79.4/20.6). The double bond distribution of the resultant internal olefins was as follows: C1 position: 0.6% by mass; C2 position: 29.5% by mass; C3 position: 25.5% by mass; C4 position: 18.9% by mass; C5 position: 11.2% by mass; C6 position: 6.8% by mass; C7 position: 3.7% by mass; and C8 and C9 positions: 3.8% by mass in total.

Production Example G

Synthesis of Internal Olefin having 12 Carbon Atoms (C2 Position: 22.7% by Mass)

Into a flask equipped with a stirrer were charged 7000 g (41.6 mol) of 1-dodecene "LINEALENE 12" (manufactured by Idemitsu Kosan Co., Ltd.), and 70 g (1% by mass of the α-olefin as the starting material) of CP814E HY Zeolite (manufactured by Zeolyst International, Inc.) as a solid acid catalyst. The olefin was caused to react under stirring at 165° C. for 5 hours while nitrogen (7000 mL/min.) was caused to flow into the system. After the end of the reaction, the conversion rate of the α-olefin was 100%. The purity of the resultant C12 internal olefin was 95.2%. The resultant crude internal olefin was placed into a flask for distillation, and distilled at 148 to 158° C. and 0.5 mmHg to yield an internal olefin having 12 carbon atoms and an olefin purity of 100%. The double bond distribution of the resultant internal olefin was as follows: C1 position: 0.1% by mass; C2 position: 22.7% by mass; C3 position: 22.2% by mass; C4 position: 21.4% by mass; C5 position: 17.3% by mass; and C6 position: 16.3% by mass.

Production Example H

Synthesis of Internal Olefin having 14 Carbon Atoms (C2 Position: 19.2% by Mass)

Into a flask equipped with a stirrer were charged 7000 g (35.6 mol) of 1-tetradecene "LINEALENE 14" (manufactured by Idemitsu Kosan Co., Ltd.), and 70 g (1% by mass of the α-olefin as the starting material) of CP814E HY Zeolite (manufactured by Zeolyst International, Inc.) as a solid acid catalyst. The olefin was caused to react under stirring at 165° C. for 5 hours while nitrogen (7000 mL/min.) was caused to flow into the system. After the end of the reaction, the conversion rate of the α-olefin was 100%. The purity of the resultant C14 internal olefin was 94.7%. The resultant crude internal olefin was placed into a flask for distillation, and distilled at 148 to 158° C. and 0.5 mmHg to yield an internal olefin having 14 carbon atoms and an olefin purity of 100%. The double bond distribution of the resultant internal olefin was as follows: C1 position: 0.4% by mass; C2 position: 19.2% by mass; C3 position: 16.6% by mass; C4 position: 22.1% by mass; C5 position: 17.1% by mass; C6 position: 12.3% by mass; and C7 position: 12.3% by mass.

<Method for Producing Internal Olefin Sulfonate>

Example 1

A thin-film sulfonation reactor was used which had an external jacket having an inside diameter of 14 mm and a length of 4 m. The internal olefins having 16 carbon atoms and 18 carbon atoms, respectively, (ratio by mass: 74.0/26.0), which were yielded in Production Example C, were caused to flow down to be made into a thin-film form at a supply rate of 2.7 L/h along the inner wall of the reactor. Simultaneously, the temperature of reactor-cooling water was adjusted to a temperature shown in Table 1, and $SO_3$ gas diluted with dehumidified air ($SO_3$ concentration therein: 1.1% by volume) was added thereto at a supply rate of 130 L/min (the ratio by mole of $SO_3$/the olefins is shown in Table 1) to conduct sulfonating reaction.

Sodium hydroxide, the ratio by mole of which to the resultant sulfonated internal olefin was set as shown in Table 1, was made into an aqueous solution having a concentration shown in Table 1. This aqueous solution was mixed with the sulfonated internal olefin at a temperature of 30° C., using a Homo Mixer (machine name: T. K. ROBOMIX, T. K. HOMO MIXER, T. K. HOMO DISPER, T. K. HOMO LINE MIL, manufactured by PRIMIX Corporation; rotary impellers: 30 mm in diameter, rotation rate: 10000 rpm, and agitating speed: shown in Table 1). After a neutralizing period shown in Table 1 elapsed, the particle diameter of oil droplets of the resultant oily product was checked. The neutralization was then ended to yield a neutralized product. The checked particle diameter of the oil droplets is shown in Table 1.

Within one hour of the end of the neutralization, the neutralized product was heated in an autoclave at a temperature of 160° C. for 1 hour to be hydrolyzed. In this way, an internal olefin sulfonate was yielded as a 50% by mass aqueous solution. The internal olefin sulfonate contained an internal olefin and an inorganic salt that each had an amount proportion shown in Table 1. The amount proportion shown in Table 1, which was a proportion of each of the internal olefin and the inorganic salt, was a proportion obtained by making a calculation using the amount of the active substances as a reference.

Examples 2 to 4

In each of the examples, the same sulfonating reaction as in Example 1 was conducted, using the C18 internal olefin yielded in Production Example B instead of the internal olefins used in Example 1. Next, in the same way as in Example 1 except conditions shown in Table 1, the resultant sulfonated internal olefin was neutralized and hydrolyzed to yield an internal olefin sulfonate as a 15% by mass aqueous solution. Table 1 shows the particle diameter of oil droplets checked before the end of the neutralization; and the amount proportion of each of an internal olefin and an inorganic salt each contained in the resultant internal olefin sulfonate.

Example 5

Internal olefin sulfonate as a 50% by mass aqueous solution were yielded in the same way as in Example 1 except the following: instead of the internal olefins used in Example 1, the C16/C18 internal olefins (ratio by mass: 79.4/20.6) yielded in Production Example F were caused to flow down to be made into a thin-film form at a supply rate of 5.6 L/h; and further the temperature of the reactor-cooling water was adjusted to a temperature shown in Table 1, and $SO_3$ gas diluted with dehumidified air ($SO_3$ concentration therein: 2.3% by volume) was added thereto at a supply rate of 300 L/min (the ratio by mole of $SO_3$/the olefins is shown in Table 1) to set conditions shown in Table 1. Table 1 shows the particle diameter of oil droplets checked before the end of the neutralization; and the amount proportion of each of an internal olefin and an inorganic salt each contained in the resultant internal olefin sulfonate.

Example 6

The same internal olefins as used in Example 5 were used, and were caused to flow down to be made into a thin-film form at a supply rate of 5.6 L/h. Simultaneously, the temperature of reactor-cooling water was adjusted to a temperature shown in Table 1, and $SO_3$ gas diluted with dehumidified air ($SO_3$ concentration therein: 2.7% by volume) was added thereto at a supply rate of 250 L/min (the ratio by mole of $SO_3$/the olefins is shown in Table 1) to conduct sulfonating reaction. The resultant sulfonated internal olefin was passed into a continuous type neutralizing reactor (in a loop form; inside diameter of a pipe: 28 mm, length of the pipe: 3.9 m, and content volume thereof: 2.4 L) at 90.0 g/min. Sodium hydroxide, the ratio by mole of which to the resultant sulfonated internal olefin was set as shown in Table 1, was made into an aqueous solution having a concentration shown in Table 1, and this aqueous solution was passed into the reactor at 92.8 g/min. A Milder Mixer (product name: MILDER MDN303V, manufactured by Matsubo Corporation; agitating speed: shown in Table 1) was then used to perform continuous neutralization (mixing temperature and neutralizing temperature: 20° C.). At this time, the mean residence time was a period shown as the neutralizing period in Table 1, and the circulatory ratio was 10 times. When the continuous neutralization was performed for 90 minutes so that the reaction system turned into a stationary state, 50 mL of the reaction liquid was collected. The particle diameter of oil droplets of the resultant oily product was then checked, and a neutralized product was yielded. Table 1 shows the particle diameter of the oil droplets.

The neutralized product was hydrolyzed under conditions shown in Table 1 in the same way as Example 1 to yield an internal olefin sulfonate as a 55% by mass aqueous solution. Table 1 shows the amount proportion of each of an internal olefin and an inorganic salt each contained in the resultant internal olefin sulfonate.

Comparative Example 1

An internal olefin sulfonate was yielded as a 15% by mass aqueous solution through hydrolysis in the same way as in Example 2 except that the neutralization was performed using a Homo Mixer at a rotation rate of 1400 rpm instead of 10000 rpm, and conditions shown in Table 1 were used. Table 1 shows the particle diameter of oil droplets checked before the end of the neutralization; and the amount proportion of each of an internal olefin and an inorganic salt each contained in the resultant internal olefin sulfonate.

Comparative Example 2

The same internal olefin as used in Example 2 was used, and passed to be made into a thin-film form at a supply rate of 5.6 L/h. Simultaneously, the temperature of reactor-cooling water was adjusted to 20° C., and $SO_3$ gas diluted with dehumidified air ($SO_3$ concentration therein: 1.8% by volume) was added thereto at a supply rate of 250 L/min (the ratio by mole of $SO_3$/the olefin is shown in Table 1) to conduct sulfonating reaction. Continuous neutralization and hydrolysis were then performed in the same way as Example 6 except the following: the resultant sulfonated internal olefin was passed into a reactor at 80.0 g/min; a sodium hydroxide aqueous solution which had a concentration shown in Table 1 was passed thereinto at 165.2 g/min; and conditions shown in Table 1 were used. In this way, an internal olefin sulfonate was yielded as a 35% by mass aqueous solution. Table 1 shows the particle diameter of oil droplets checked; and the amount proportion of each of an internal olefin and an inorganic salt each contained in the resultant internal olefin sulfonate.

Comparative Example 3

The same internal olefins as used in Example 1 were used to attain sulfonation, neutralization and hydrolysis in the same way as Example 1 except that conditions shown in Table 1 were used. In this way, an internal olefin sulfonate was yielded as a 50% by mass aqueous solution. Table 1 shows the particle diameter of oil droplets checked; and the amount proportion of each of an internal olefin and an inorganic salt each contained in the resultant internal olefin sulfonate.

Example 7

The same internal olefins as used in Example 1 were used to attain sulfonation, neutralization and hydrolysis in the same way as Example 1 except that conditions shown in Table 2 were used. In this way, an internal olefin sulfonate was yielded as a 35% by mass aqueous solution. Table 2 shows the particle diameter of oil droplets checked; and the amount proportion of each of an internal olefin and an inorganic salt each contained in the resultant internal olefin sulfonate.

Example 8

The same internal olefins as used in Example 1 were used to attain sulfonation, neutralization and hydrolysis in the same way as Example 1 except that conditions shown in Table 2 were used. In this way, an internal olefin sulfonate was yielded as a 45% by mass aqueous solution. Table 2 shows the particle diameter of oil droplets checked; and the amount proportion of each of an internal olefin and an inorganic salt each contained in the resultant internal olefin sulfonate.

Example 9

The same internal olefins as used in Example 5 were used to conduct the same sulfonating reaction as in Example 6. Next, in the same way as in Example 1 except that conditions shown in Table 2 were used, the resultant sulfonated internal olefin was neutralized and hydrolyzed to yield an internal olefin sulfonate as a 68% by mass aqueous solution. Table 2 shows the particle diameter of oil droplets checked; and the amount proportion of each of an internal olefin and an inorganic salt each contained in the resultant internal olefin sulfonate.

Example 10

The same internal olefins as used in Example 5 were used to attain sulfonation, neutralization and hydrolysis in the same way as Example 9 except that conditions shown in Table 2 were used. In this way, an internal olefin sulfonate was yielded as a 72% by mass aqueous solution. Table 2 shows the particle diameter of oil droplets checked; and the amount proportion of each of an internal olefin and an inorganic salt each contained in the resultant internal olefin sulfonate.

Examples 11 and 12

The same internal olefins as used in Example 1 were used to attain sulfonation, neutralization and hydrolysis in the same way as Example 1 except that conditions shown in Table 2 were used. In this way, an internal olefin sulfonate was yielded as a 50% by mass aqueous solution. Table 2 shows the particle diameter of oil droplets checked; and the amount proportion of each of an internal olefin and an inorganic salt each contained in the resultant internal olefin sulfonate.

Examples 13 to 15

The same internal olefins as used in Example 5 were used to attain sulfonation, continuous neutralization and hydrolysis in the same way as Example 6 except that conditions shown in Table 3 were used. In this way, an internal olefin sulfonate was yielded as a 55% by mass aqueous solution. Table 3 shows the particle diameter of oil droplets checked; and the amount proportion of each of an internal olefin and an inorganic salt each contained in the resultant internal olefin sulfonate.

Examples 16 to 18

The same internal olefins as used in Example 5 were used to attain sulfonation, neutralization and hydrolysis in the same way as Example 9 except that conditions shown in Table 3 were used. In this way, an internal olefin sulfonate was yielded as a 50% by mass aqueous solution. Table 3 shows the particle diameter of oil droplets checked; and the amount proportion of each of an internal olefin and an inorganic salt each contained in the resultant internal olefin sulfonate.

Example 19

The C12 internal olefin yielded in Production Example G was used to attain sulfonation, neutralization and hydrolysis in the same way as Example 1 except that conditions shown in Table 3 were used. In this way, an internal olefin sulfonate was yielded as a 50% by mass aqueous solution. Table 3 shows the particle diameter of oil droplets checked; and the amount proportion of each of an internal olefin and an inorganic salt each contained in the resultant internal olefin sulfonate.

Example 20

The C14 internal olefin yielded in Production Example H was used to attain sulfonation, neutralization and hydrolysis in the same way as Example 1 except that conditions shown in Table 3 were used. In this way, an internal olefin sulfonate was yielded as a 50% by mass aqueous solution. Table 3 shows the particle diameter of oil droplets checked; and the amount proportion of each of an internal olefin and an inorganic salt each contained in the resultant internal olefin sulfonate.

Example 21

The same internal olefins as used in Example 5 were used to attain sulfonation, neutralization and hydrolysis in the same way as Example 14 except that conditions shown in Table 4 were used. In this way, an internal olefin sulfonate was yielded as a 55% by mass aqueous solution. Table 4 shows the particle diameter of oil droplets checked; and the amount proportion of each of an internal olefin and an inorganic salt each contained in the resultant internal olefin sulfonate.

Example 22

The same internal olefin as used in Example 2 was used to attain sulfonation, continuous neutralization and hydrolysis in the same way as Example 6 except that conditions shown in Table 4 were used. In this way, an internal olefin sulfonate was yielded as a 40% by mass aqueous solution. Table 4 shows the particle diameter of oil droplets checked; and the amount proportion of each of an internal olefin and an inorganic salt each contained in the resultant internal olefin sulfonate.

Example 23

The same internal olefin as used in Example 2 was used to attain sulfonation, neutralization and hydrolysis in the same way as Example 22 except that conditions shown in Table 4 were used. In this way, an internal olefin sulfonate was yielded as a 40% by mass aqueous solution. Table 4 shows the particle diameter of oil droplets checked; and the amount proportion of each of an internal olefin and an inorganic salt each contained in the resultant internal olefin sulfonate.

TABLE 1

| | | Examples | | | | | | Comparative Examples | | |
|---|---|---|---|---|---|---|---|---|---|---|
| | | 1 | 2 | 3 | 4 | 5 | 6 | 1 | 2 | 3 |
| Internal olefin | The number of carbon atoms | C16/C18 | C18 | C18 | C18 | C16/C18 | C16/C18 | C18 | C18 | C16/C18 |
| | Ratio by mass (C16/C18) | 74.0/26.0 | 0/100 | 0/100 | 0/100 | 79.4/20.6 | 79.4/20.6 | 0/100 | 0/100 | 74.0/26.0 |
| | Double bond (% by mass) at C2 position | 16.6 | 16.9 | 16.9 | 16.9 | 29.5 | 29.5 | 16.9 | 16.9 | 16.6 |
| Sulfonating step | Reaction ratio by mole of SO3/olefin | 1.03 | 1.03 | 1.03 | 1.03 | 1.02 | 1.01 | 1.03 | 1.02 | 1.03 |
| | Cooling water temperature (° C.) | 10 | 10 | 10 | 10 | 20 | 10 | 10 | 20 | 10 |
| Neutralizing step | Concentration (% by mass) in aqueous alkaline solution | 13.5 | 5.2 | 5.2 | 24.9 | 11.6 | 13.5 | 5.2 | 7.1 | 13.5 |
| | Alkali/sulfonated internal olefin (ratio by mole) | 1.25 | 2.5 | 2.5 | 1.5 | 1.07 | 1.04 | 2.5 | 1.25 | 1.25 |
| | Temperature (° C.) at mixing and neutralizing times | 30 | 30 | 30 | 30 | 30 | 20 | 30 | 60 | 30 |
| | Neutralizing mixer | Homo Mixer | Homo Mixer | Homo Mixer | Homo Mixer | Homo Mixer | Milder | Homo Mixer | Milder | Homo Mixer |
| | Agitating speed (m/s) | 15.7 | 15.7 | 7.9 | 15.7 | 15.7 | 23.6 | 2.2 | 23.6 | 2.2 |
| | Neutralizing period (minutes) | 15 | 15 | 15 | 15 | 15 | 13 | 15 | 26 | 15 |
| | Sulfonated internal olefin concentration (%) | 50 | 15 | 15 | 60 | 50 | 55 | 15 | 35 | 50 |
| | Oil droplet particle diameter (μm) | 3.8 | 2.0 | 6.5 | 2.0 | 4.0 | 1.7 | 18 | 0.4 | 16.4 |
| Hydrolyzing step | Temperature (° C.) | 160 | 160 | 160 | 160 | 160 | 160 | 160 | 160 | 160 |
| | Reaction period (minutes) | 60 | 60 | 60 | 60 | 60 | 60 | 60 | 60 | 60 |
| Evaluation | Internal olefin (% by mass) | 1.0 | 1.2 | 3.8 | 0.7 | 3.6 | 1.3 | 11.0 | 5.3 | 9.7 |
| | Inorganic salt (% by mass) | 2.0 | 3.3 | 5.8 | 1.7 | 2.9 | 1.9 | 7.8 | 6.8 | 7.9 |

TABLE 2

| | | Examples | | | | | | Examples | |
|---|---|---|---|---|---|---|---|---|---|
| | | 7 | 8 | 1 | 9 | 10 | 11 | 1 | 12 |
| Internal olefin | The number of carbon atoms | C16/C18 | C16/C18 | C16/C18 | C16/C18 | C16/C18 | C16/C18 | C16/C18 | C16/C18 |
| | Ratio by mass (C16/C18) | 74.0/26.0 | 74.0/26.0 | 74.0/26.0 | 79.4/20.6 | 79.4/20.6 | 74.0/26.0 | 74.0/26.0 | 74.0/26.0 |
| | Double bond (% by mass) at C2 position | 16.6 | 16.6 | 16.6 | 29.5 | 29.5 | 16.6 | 16.6 | 16.6 |

TABLE 2-continued

|  |  | Examples |  |  |  |  | Examples |  |  |
|---|---|---|---|---|---|---|---|---|---|
|  |  | 7 | 8 | 1 | 9 | 10 | 11 | 1 | 12 |
| Sulfonating step | Reaction ratio by mole of SO3/olefin | 1.03 | 1.03 | 1.03 | 1.01 | 1.01 | 1.03 | 1.03 | 1.03 |
|  | Cooling water temperature (° C.) | 10 | 10 | 10 | 10 | 10 | 10 | 10 | 10 |
| Neutralizing step | Concentration (% by mass) in aqueous alkaline solution | 7.4 | 10.9 | 13.5 | 22.1 | 25.7 | 13.5 | 13.5 | 13.5 |
|  | Alkali/sulfonated internal olefin (ratio by mole) | 1.25 | 1.25 | 1.25 | 1.1 | 1.1 | 1.25 | 1.25 | 1.25 |
|  | Temperature (° C.) at mixing and neutralizing times | 30 | 30 | 30 | 30 | 30 | 30 | 30 | 40 |
|  | Neutralizing mixer | Homo Mixer | Homo Mixer | Homo Mixer | Homo Mixer | Homo Mixer | Homo Mixer | Homo Mixer | Homo Mixer |
|  | Agitating speed (m/s) | 15.7 | 15.7 | 15.7 | 15.7 | 15.7 | 7.9 | 15.7 | 15.7 |
|  | Neutralizing period (minutes) | 15 | 15 | 15 | 5 | 5 | 15 | 15 | 15 |
|  | Sulfonated internal olefin concentration (%) | 35 | 45 | 50 | 68 | 72 | 50 | 50 | 50 |
|  | Oil droplet particle diameter (μm) | 5.2 | 4.2 | 3.8 | 1.8 | 1.7 | 7.1 | 3.8 | 3.2 |
| Hydrolyzing step | Temperature (° C.) | 160 | 160 | 160 | 160 | 160 | 160 | 160 | 160 |
|  | Reaction period (minutes) | 60 | 60 | 60 | 60 | 60 | 60 | 60 | 60 |
| Evaluation | Internal olefin (% by mass) | 4.3 | 1.7 | 1.0 | 1.3 | 1.9 | 3.9 | 1.0 | 4.2 |
|  | Inorganic salt (% by mass) | 5.6 | 2.6 | 2.0 | 1.8 | 2.7 | 4.6 | 2.0 | 5.3 |

TABLE 3

|  |  | Examples |  |  |  | Examples |  |  | Examples |  |
|---|---|---|---|---|---|---|---|---|---|---|
|  |  | 13 | 6 | 14 | 15 | 16 | 17 | 18 | 19 | 20 |
| Internal olefin | The number of carbon atoms | C16/C18 | C16/C18 | C16/C18 | C16/C18 | C16/C18 | C16/C18 | C16/C18 | C12 | C14 |
|  | Ratio by mass (C16/C18) | 79.4/20.6 | 79.4/20.6 | 79.4/20.6 | 79.4/20.6 | 79.4/20.6 | 79.4/20.6 | 79.4/20.6 | — | — |
|  | Double bond (% by mass) at C2 position | 29.5 | 29.5 | 29.5 | 29.5 | 29.5 | 29.5 | 29.5 | 22.7 | 19.2 |
| Sulfonating step | Reaction ratio by mole of SO3/olefin | 1.01 | 1.01 | 1.01 | 1.01 | 1.01 | 1.01 | 1.01 | 1.03 | 1.03 |
|  | Cooling water temperature (° C.) | 10 | 10 | 10 | 10 | 10 | 10 | 10 | 10 | 10 |
| Neutralizing step | Concentration (% by mass) in aqueous alkaline solution | 13.5 | 13.5 | 13.5 | 13.5 | 11.5 | 11.5 | 11.5 | 16.6 | 15.4 |
|  | Alkali/sulfonated internal olefin (ratio by mole) | 1.04 | 1.04 | 1.04 | 1.04 | 1.1 | 1.1 | 1.1 | 1.25 | 1.25 |
|  | Temperature (° C.) at mixing and neutralizing times | 30 | 20 | 20 | 20 | 30 | 30 | 30 | 30 | 30 |
|  | Neutralizing mixer | Milder | Milder | Milder | Milder | Homo Mixer | Homo Mixer | Homo Mixer | Homo Mixer | Homo Mixer |
|  | Agitating speed (m/s) | 23.6 | 23.6 | 14.1 | 5.0 | 15.7 | 15.7 | 15.7 | 15.7 | 15.7 |
|  | Neutralizing period (minutes) | 13 | 13 | 13 | 13 | 5 | 30 | 90 | 15 | 15 |
|  | Sulfonated internal olefin concentration (%) | 55 | 55 | 55 | 55 | 50 | 50 | 50 | 50 | 50 |
|  | Oil droplet particle diameter (μm) | 0.9 | 1.7 | 1.9 | 2.3 | 5.5 | 2.6 | 1.4 | 0.3 | 1.2 |
| Hydrolyzing step | Temperature (° C.) | 160 | 160 | 160 | 160 | 160 | 160 | 160 | 160 | 160 |
|  | Reaction period (minutes) | 60 | 60 | 60 | 60 | 60 | 60 | 60 | 60 | 60 |
| Evaluation | Internal olefin (% by mass) | 1.4 | 1.3 | 1.5 | 1.6 | 2.5 | 2.3 | 1.8 | 1.7 | 3.9 |
|  | Inorganic salt (% by mass) | 2.1 | 1.9 | 2.0 | 2.4 | 1.9 | 2.8 | 2.2 | 3.1 | 2.1 |

TABLE 4

|  |  | Examples |  |  |  |
|---|---|---|---|---|---|
|  |  | 14 | 21 | 22 | 23 |
| Internal olefin | The number of carbon atoms | C16/C18 | C16/C18 | C18 | C18 |
|  | Ratio by mass(C16/C18) | 79.4/20.6 | 79.4/20.6 | 0/100 | 0/100 |
|  | Double bond (% by mass) at C2 position | 29.5 | 29.5 | 16.9 | 16.9 |

TABLE 4-continued

| | | Examples | | | |
|---|---|---|---|---|---|
| | | 14 | 21 | 22 | 23 |
| Sulfonating step | Reaction ratio by mole of SO3/olefin | 1.01 | 1.01 | 1.02 | 1.02 |
| | Cooling water temperature (° C.) | 10 | 10 | 10 | 10 |
| Neutralizing step | Concentration (% by mass) in aqueous alkaline solution | 13.5 | 13.5 | 8.6 | 8.6 |
| | Alkali/sulfonated internal olefin (ratio by mole) | 1.04 | 1.04 | 1.2 | 1.2 |
| | Temperature (° C.) at mixing and neutralizing times | 20 | 20 | 20 | 20 |
| | Neutralizing mixer | Milder | Homo Mixer | Milder | Homo Mixer |
| | Agitating speed(m/s) | 14.1 | 14.1 | 23.6 | 23.6 |
| | Neutralizing period (minutes) | 13 | 13 | 13 | 13 |
| | Sulfonated internal olefin concentration (%) | 55 | 55 | 40 | 40 |
| | Oil droplet particle diameter (μm) | 1.9 | 2.4 | 3.2 | 3.7 |
| Hydrolyzing step | Temperature (° C.) | 160 | 160 | 160 | 160 |
| | Reaction period (minutes) | 60 | 60 | 60 | 60 |
| Evaluation | Internal olefin (% by mass) | 1.5 | 1.9 | 2.7 | 2.9 |
| | Inorganic salt (% by mass) | 2.0 | 2.3 | 2.2 | 2.5 |

As is clear from Tables 1 to 4, in each of Examples 1 to 23, in which in the state that the temperature at the time of each of the mixing and the neutralization was kept at 40° C. or lower, the particle diameter of the oil droplets of the oily product was adjusted to 10 μm or less, the internal olefin sulfonate was obtainable which was smaller in internal olefin content and inorganic salt content by percentage as compared with Comparative Examples 1 and 3, in each of which the particle diameter of the oil droplets was out of the range for the value thereof, and with Comparative Example 2, in which the temperature at the time of each of the mixing and the neutralization was out of the range for the value thereof.

INDUSTRIAL APPLICABILITY

An internal olefin sulfonate according to the present invention is useful as a basic agent of a washing agent.

The invention claimed is:

1. A method for producing an internal olefin sulfonate, comprising:
    causing an internal olefin to react with sulfur trioxide to yield a sulfonated internal olefin;
    mixing the sulfonated internal olefin with an aqueous alkaline solution at 40° C. or lower to yield a mixture, and applying a shearing force to the mixture at an agitating speed of 5 m/s or more until a particle diameter of oil droplets of an oily product of the mixture turns to 10 μm or less to yield a neutralized product; and
    hydrolyzing the neutralized product.

2. The method for producing an internal olefin sulfonate according to claim 1, wherein concentration of the sulfonated internal olefin in the neutralized product is from 15 to 75% by mass.

3. The method for producing an internal olefin sulfonate according to claim 1, wherein a means for applying the shearing force is an agitating machine.

4. The method for producing an internal olefin sulfonate according to claim 3, wherein agitating speed of the agitating machine is from 5 to 30 m/s.

5. The method for producing an internal olefin sulfonate according to claim 1, wherein a total time of the steps of mixing and applying shearing force is from 5 to 100 minutes.

6. The method for producing an internal olefin sulfonate according to claim 1, wherein the internal olefin comprises 48% or less by mass of an internal olefin isomer which has, at a C2 position thereof, a double bond.

7. The method for producing an internal olefin sulfonate according to claim 1, wherein the mixing of the sulfonated internal olefin with the aqueous alkaline solution is performed at from 0 to 35° C.

8. The method for producing an internal olefin sulfonate according to claim 1, wherein the particle diameter of oil droplets of the oily product is 0.1 μm or more.

9. The method for producing an internal olefin sulfonate according to claim 1, wherein concentration of the sulfonated internal olefin in the neutralized product is from 30 to 75% by mass.

10. The method for producing an internal olefin sulfonate according to claim 1, wherein in the neutralizing step, concentration of the sulfonated internal olefin in the neutralized product is from 40 to 70% by mass.

11. The method for producing an internal olefin sulfonate according to claim 1, wherein the internal olefin is caused to react with the sulfur trioxide to yield the sulfonated internal olefin reactor, and
    temperature of a cooling water of the reactor is from 0 to 20° C.

12. The method for producing an internal olefin sulfonate according claim 1, wherein the steps of mixing and applying shearing force are performed by a continuous method.

13. The method for producing an internal olefin sulfonate according to claim 12, wherein the steps of mixing and applying shearing force are conducted in a loop-type reactor.

14. The method for producing an internal olefin sulfonate according to claim 12, wherein a circulatory ratio of a reaction liquid circulating in a reactor to an amount of a flowing amount of the reaction liquid charged into the reactor is from 3 to 30 times.

15. The method for producing an internal olefin sulfonate according to claim 1, wherein the agitating speed is from 5 to 30 m/s.

* * * * *